United States Patent
Tobey

(10) Patent No.: US 9,976,159 B2
(45) Date of Patent: May 22, 2018

(54) METHODS FOR CONTROLLING ACETOCLASTIC MICROORGANISMS IN ACETOGENIC SYNGAS FERMENTATION PROCESSES

(71) Applicant: Richard Tobey, St. Charles, IL (US)

(72) Inventor: Richard Tobey, St. Charles, IL (US)

(73) Assignee: Synata Bio, Inc., Warrenville, IL (US)

( * ) Notice: Subject to any disclaimer, the term of this patent is extended or adjusted under 35 U.S.C. 154(b) by 432 days.

(21) Appl. No.: 14/515,250

(22) Filed: Oct. 15, 2014

(65) Prior Publication Data

US 2016/0108439 A1    Apr. 21, 2016

(51) Int. Cl.
*C12P 7/06* (2006.01)
*C12P 7/14* (2006.01)
*C12P 7/16* (2006.01)
*C12P 39/00* (2006.01)

(52) U.S. Cl.
CPC .......... *C12P 7/14* (2013.01); *C12P 7/065* (2013.01); *C12P 7/16* (2013.01); *C12P 39/00* (2013.01); *Y02E 50/10* (2013.01); *Y02E 50/17* (2013.01)

(58) Field of Classification Search
USPC ........................................ 435/161, 160, 162
IPC ........................................ C12P 7/06,7/14, 7/16
See application file for complete search history.

(56) References Cited

U.S. PATENT DOCUMENTS

| 8,771,999 B2 * | 7/2014 | Hickey | C12P 7/00 435/132 |
| 8,936,927 B2 * | 1/2015 | Hickey | C12P 7/06 435/245 |
| 9,034,617 B2 * | 5/2015 | Hickey | C12P 7/16 435/157 |
| 9,469,860 B2 * | 10/2016 | Enzien | C12P 7/16 |
| 9,528,130 B2 * | 12/2016 | Datta | C12P 7/16 |

* cited by examiner

*Primary Examiner* — Louise W Humphrey
*Assistant Examiner* — Kailash C Srivastava
(74) *Attorney, Agent, or Firm* — Cardinal Law Group

(57) ABSTRACT

Methods are disclosed for controlling the population of acetoclastic microorganisms in a process for the bioconversion of gas substrate comprising at least one of CO and a mixture of $CO_2$ and hydrogen to at least one oxygenated organic compound by contact of said gas substrate under acidic, anaerobic fermentation conditions in a bioreactor containing an aqueous fermentation broth having a population of at least one acetogenic microorganism for bioconverting said gas substrate to at least one acetogenic oxygenated organic compound, said fermentation zone defining a head space, said methods comprising continuously or intermittently controlling the partial pressure of carbon dioxide in the head space to provide a desired population ratio of acetoclastic microorganisms to acetogenic microorganisms.

13 Claims, No Drawings

METHODS FOR CONTROLLING ACETOCLASTIC MICROORGANISMS IN ACETOGENIC SYNGAS FERMENTATION PROCESSES

FIELD OF THE INVENTION

This invention pertains to methods for controlling the population of acetoclastic microorganisms in acetogenic syngas fermentation processes to produce oxygenated organic compound and processes for acetogenic syngas fermentation using the methods.

BACKGROUND

Anaerobic fermentations of hydrogen and carbon monoxide to oxygenated organic compounds involve the contact of the substrate gas in an aqueous fermentation broth with microorganisms that use the Wood Ljungdahl pathway. The theoretical equations for the conversion of carbon monoxide and hydrogen to ethanol are:

$$6CO+3H_2O.C_2H_5OH+4CO_2$$

$$6H_2+2CO_2.C_2H_5OH+3H_2O.$$

As can be seen, the conversion of carbon monoxide results in the generation of carbon dioxide. The conversion of hydrogen involves the consumption of hydrogen and carbon dioxide, and this conversion is sometimes referred to as the $H_2/CO_2$ conversion. For purposes herein, it is referred to as the hydrogen conversion. The microorganisms for such anaerobic fermentations are acetogenic microorganisms. These microorganisms are typically grown on defined, minimal media (approaching autotrophic media).

Anaerobic fermentations offer the potential to provide oxygenated organic compounds at attractive costs, and to enhance economics, the fermentations should be practiced on a large scale in a continuous mode. Currently world-class ethanol production facilities have capacities in excess of 100,000,000 gallons per year. Commercial-scale bioreactors are at least 1 million, and more often at least about 5 to 25 million liters. An ethanol production facility typically contains a plurality of these commercial-scale bioreactors. It is axiomatic that the fermentations provide good selectivity to the sought oxygenated organic compound from the substrate gas (syngas) for economic reasons as well as to facilitate the recovery and purification of an oxygenated organic compound meeting specifications. This good selectivity should be retained over extended periods of time of continuous operation.

One of the potential problems that can be faced by a continuous, commercial facility for the bioconversion of syngas to oxygenated organic compound is contamination of the fermentation broth with an undesirable population of microorganisms. These contaminating microorganisms can bioconvert one or more of the components in the syngas or products or byproducts of the acetogenic bioconversion to undesired oxygenated organic compounds. Accordingly the contaminated microorganisms can deleteriously affect the conversion efficiency to the sought oxygenated organic compound and/or the achieving a product of the oxygenated organic compound that meets purity specifications. Exclusion of contaminating microorganisms from commercial scale bioreactors can be challenging and costly. Even with steam cleaning, finite chances exist that a microorganism may escape the sterilization process or may contaminate a previously cleaned area of the bioreactor prior to completion of the sterilization or be contained in materials introduced into the bioreactor during the bioconversion process. Moreover, if a commercial-scale bioreactor becomes contaminated with undue populations of other microorganisms, the remedy is costly in that the bioreactor must be taken off-line, its contents discharged with appropriate waste treatment, and the bioreactor recharged, usually requiring an extended duration of time to reestablish a suitable microorganism population for commercial production.

Fortunately, since syngas is the principal energy source for the acetogenic microorganisms, aerobic microorganisms are eliminated, and the redox potential of the fermentation broth is sufficiently low to restrict the growth of facultative microorganisms. Additionally, the typical pH used for the acetogenic fermentation is generally low enough, e.g., below about 5.5 or 6, to restrict methanogenic microorganisms. As a result, there are very few species of microorganisms which can survive, let alone thrive within an acetogenic fermentation system. The two notable exceptions are the heteroacetogens and acetoclastic microorganisms. Heteroacetogens are microorganisms that contain both the Wood Ljundahl pathway, as well as butyryl (or higher) CoA. Acetoclastic microorganisms are those which are able to use acetate anion and/or acetate and ethanol to produce butyrate and/or higher organic anions.

Where ethanol is the desired product from syngas fermentation, heteroacetogens can often be tolerated or controlled even in continuous processes that operate for extended periods of time. In contrast, since acetogenic microorganisms, including those for the bioconversion of syngas to ethanol, produce measurable amounts of acetic acid, in practice, is difficult to restrict the presence and/or growth of the population of acetoclastic microorganisms.

In some bioconversion processes both acetogenic and acetoclastic microorganisms are used for symbiotic fermentations. For instance, mixed cultures of anaerobic microorganisms can be used to bioconvert syngas to higher alcohols and mixtures of alcohols. See, for instance, United States Published Patent Application 20140206052 A1 and 20140206066 A1; U.S. patent application Ser. No. 13/802,916, filed Mar. 14, 2013, entitled Method for production of n-propanol and other C3-carbon containing products from syngas by symbiotic arrangement of C1-fixing and C3-producing anaerobic microorganism cultures (Toby, et al.); Ser. No. 13/802,930, filed Mar. 14, 2013, entitled method for production of n-propanol and/or ethanol by fermentation of multiple substrates in a symbiotic manner (Enzein, et al.); Ser. No. 13/802,924, filed Mar. 14, 2013, entitled Method for production of n-propanol and other C3-containing products from syngas using membrane supported bioreactor (Datta, et al.) and Ser. No. 13/802,905, filed Mar. 14, 2013, entitled Method for production of n-propanol and other C3-containing products from syngas by symbiotic co-cultures of anaerobic microorganisms (Datta, et al.).

These processes rely upon an appropriate balance between acetogenic microorganism and acetoclastic microorganisms to obtain the desired product slate. Maintaining this balance in continuous fermentation processes represents a significant challenge particularly for commercial scale bioreactors that are expected to be operated over extended durations, often, at least about one year of continuous operation.

Accordingly methods are sought to selectively control the population of acetoclastic microorganisms in acetogenic fermentations of syngas. The desired methods should be efficacious for the selective production of oxygenated organic compound and for the syntrophic bioconversions of syngas using mixtures of acetoclastic microorganisms and acetogenic microorganisms. Advantageously, the methods should not result in undue operating expenses for the bioconversion processes or loss of bioconversion efficiency.

SUMMARY

By this invention it has been found that the partial pressure of carbon dioxide in a bioreactor can be varied to selectively affect the population of acetoclastic microorganisms in anaerobic fermentation processes using acetogenic microorganisms for the bioconversions of syngas to oxygenated organic compounds. A population of microorganisms means the active cells of the microorganism in a bioreactor. Lower carbon dioxide partial pressures are adverse to the acetoclastic microorganisms, and at low partial pressures, e.g., below about 2, say, below about 1 or 1.5, kPa, the acetoclastic microorganism population is controlled to a level where little, if any, bioconversion of acetate and ethanol produced by the acetogenic microorganisms occurs. The methods of this invention are applicable to bioconversion processes to produce oxygenated organic compounds by acetogens, e.g., acetogens to produce ethanol and/or acetate anion and acetogens that produce higher oxygenated organic compounds such as propanol, propionate anion butanol, butyrate anion, and the like, where coproduction of higher oxygenates are minimized as well as to bioconversion processes to produce mixed alcohols and higher alcohols by syntrophic fermentations using both acetogenic and acetoclastic microorganisms. The oxygenated organic compounds produced by the acetogenic microorganisms are herein referred to as the acetogenic oxygenated organic compounds, and those produced by the acetoclastic microorganisms are referred to as higher oxygenated organic compounds.

The ability of carbon dioxide concentration to effectively control the relative population of acetoclastic microorganisms to acetogenic microorganisms is particularly unexpected in that (i) acetoclastic microorganisms are capable of converting acetogenic oxygenated organic compounds contained in the fermentation broth and (ii) the bioconversion of syngas containing carbon monoxide by the acetogenic microorganisms results in the coproduction of carbon dioxide.

In one broad aspect, this invention pertains to methods for controlling the population of acetoclastic microorganisms in a process for the bioconversion of gas substrate comprising at least one of CO and a mixture of $CO_2$ and hydrogen to at least one oxygenated organic compound by contact of said gas substrate under acidic, anaerobic fermentation conditions in a bioreactor containing an aqueous fermentation broth having a population of at least one acetogenic microorganism for bioconverting said gas substrate to at least one acetogenic oxygenated organic compound, said fermentation zone defining a head space, said method comprising continuously or intermittently controlling the partial pressure of carbon dioxide in the head space to provide a desired population ratio of acetoclastic microorganisms to acetogenic microorganisms.

Another broad aspect of this invention pertains to continuous processes for the anaerobic bioconversion of a gas substrate comprising carbon monoxide, hydrogen and carbon dioxide in an aqueous fermentation broth containing acetogenic microorganisms suitable for converting said substrate to acetogenic oxygenated organic compound and, optionally, containing acetoclastic microorganisms, which processes comprise: continuously contacting said gas substrate with said aqueous broth under acidic, anaerobic fermentation conditions to bioconvert gas substrate to oxygenated organic compound and provide an oxygenated organic compound-containing broth and a depleted gas phase; continuously withdrawing the depleted gas phase from said broth; and continuously or intermittently withdrawing a portion of said broth for recovery of said oxygenated organic compound, said withdrawal being sufficient to maintain the oxygenated organic compound in said broth below a concentration that unduly adversely affects the acetogenic microorganisms, in which processes the partial pressure of carbon dioxide in the depleted gas phase from the broth is continuously or intermittently at a partial pressure of less than about 2, preferably less than about 1 or 1.5, kPa.

A yet further broad aspect of this invention pertains to continuous, syntrophic processes for the anaerobic bioconversion of a gas substrate comprising carbon monoxide, hydrogen and carbon dioxide in an aqueous fermentation broth containing a mixture of acetoclastic microorganisms and acetogenic microorganisms suitable for converting said substrate to a mixture of oxygenated organic compounds, which processes comprise: continuously contacting said gas substrate with said broth under acidic, anaerobic fermentation conditions to bioconvert syntrophicly gas substrate to said mixture of oxygenated organic compounds and provide an oxygenated organic compounds-containing broth and a depleted gas phase; continuously withdrawing the depleted gas phase from said aqueous broth; and continuously or intermittently withdrawing a portion of said broth for recovery of said oxygenated organic compounds, said withdrawal being sufficient to maintain the oxygenated organic compounds in said broth below a concentration that unduly adversely affects the acetoclastic microorganisms and acetogenic microorganisms, in which processes the partial pressure of carbon dioxide in the depleted gas phase from the broth is continuously or intermittently controlled to provide a desired mixture of oxygenated organic compounds in said broth.

In the broad aspects of this invention, the partial pressure of carbon dioxide in the depleted gas phase can be controlled by one or more suitable techniques including, but not limited to, one or more of adjusting the total pressure in the head space above the broth; adjusting the concentration of carbon dioxide in the gas substrate or otherwise adjusting the electron to carbon ratio ($e^-$ to C) of the gas substrate; and adjusting the concentration of at least one inert gas such as methane and nitrogen, in the head space or in the gas substrate.

DETAILED DISCUSSION

All patents, published patent applications, patent applications and articles referenced herein are hereby incorporated by reference in their entireties.

Definitions

As used herein, the following terms have the meanings set forth below unless otherwise stated or clear from the context of their use.

The use of the terms "a" and "an" is intended to include one or more of the element described.

Oxygenated organic compound means one or more organic compounds containing two to six carbon atoms selected from the group of aliphatic carboxylic acids and salts, alkanols and alkoxide salts, and aldehydes. Often oxygenated organic compound is a mixture of organic compounds, especially with syntrophic fermentations, produced by the microorganisms contained in the fermentation broth.

Biomass means biological material living or recently living plants and animals and contains at least hydrogen, oxygen and carbon. Biomass typically also contains nitrogen, phosphorus, sulfur, sodium and potassium. The chemical composition of biomass can vary from source to source and even within a source. Sources of biomass include, but are not limited to, harvested plants such as wood, grass clippings and yard waste, switchgrass, corn (including corn stover), hemp, sorghum, sugarcane (including bagas), and the like; and waste such as garbage and municipal waste. Biomass does not include fossil fuels such as coal, natural gas, and petroleum.

A bioreactor assembly is an assembly of one or more vessels suitable to contain aqueous broth and microorganisms for the bioconversion and can contain associated equipment such as injectors, recycle loops, agitators, and the like.

Electron to carbon ratio is calculated as the quotient of the quantity of two times the sum of the concentrations of carbon monoxide and hydrogen divided by quantity of the sum of the concentrations of carbon monoxide and carbon dioxide:

$$e^-/C=2([CO]+[H_2])/([CO]+[CO_2]).$$

The abbreviation ppm means parts per million. Unless otherwise stated or clear from the context, ppm is on a mole basis (ppm (mole)).

Aqueous broth, or aqueous fermentation broth, means a liquid water phase which may contain dissolved compounds including, but not limited to hydrogen, carbon monoxide, and carbon dioxide.

Intermittently means from time to time and may be at regular or irregular time intervals.

A concentration of the oxygenated organic compound below that which unduly adversely affects the rate of growth of the culture of microorganisms will depend upon the type of microorganism and the oxygenated organic compound. An unduly adverse effect on the growth rate means that a significant, usually at least a 20 percent, decrease in the growth rate of the microorganisms is observed in comparison to the growth rate observed in an aqueous broth having about 10 grams per liter oxygenated organic compound therein, all other parameters being substantially the same.

Substantial uniformity in liquid phase means that the oxygenated organic compound concentration in the liquid phase is substantially the same throughout a bioreactor. Usually the concentration of the oxygenated organic compound is within about 0.2 mole percentage points in a uniform liquid phase.

Substantial non-uniformity of substrate means that the concentration (both in the gas bubbles and dissolved) of at least one component provided by the gas substrate changes by at least 50 percent between the point of entry of the gas into a bioreactor and the point that the gas emerges from the aqueous fermentation broth.

Deep tank bioreactor is a bioreactor having a depth of at least about 10 meters and can be operated to provide a substantial non-uniform substrate composition over the depth of the aqueous broth contained in the bioreactor. The term bubble column bioreactor as used herein refers to a deep tank bubble column bioreactor unless otherwise explicitly stated and include deep tank reactors where the gas is introduced as small bubbles to promote mixing.

Stable gas-in-liquid dispersion means a mixture of gas bubbles in liquid where the bubbles predominantly flow in the same direction as the liquid currents in the bioreactor and may cause currents in the bioreactor, and the dispersion is sufficiently stable that it exists throughout the aqueous broth.

Syngas means a gas containing at least one of hydrogen and carbon monoxide and optionally, and usually does, contain carbon dioxide.

Syntrophic refers to the association of two or more different types (e.g. organisms, populations, strains, species, genera, families, etc.) of anaerobic microorganisms which are capable of forming a tightly associated metabolic relationship.

Co-culture of microorganisms refers to joint incubation or incubation together, of the syntrophic microorganisms. In the context of the present invention, the co-culture does not require cellular population growth during the joint incubation of the syntrophic microorganisms.

A syntrophic C3-producing microorganism is a microorganism capable of growing on ethanol and/or acetate as its primary carbon source to produce oxygenated organic compounds having three carbon atoms.

A syntrophic C4-producing microorganism is a butyrogen capable of growing on acetogenic oxygenated organic compounds as its primary carbon source. Butyrogens are any microorganism capable of converting syngas intermediates, such as ethanol and acetate and some hydrogen, to primarily n-butyrate. Butyrogens use at least one of two distinct pathways for butyrate production—the Butyrl CoA Acetyl Transferase pathway (BuCoAAT) and the Butyrl Kinase (BuK) pathway. The BuCoAAT pathway converts butyrl CoA to butyrate through the BuCoAAT enzyme while the BuK pathway converts butyryl CoA through a BuK enzyme.

Selectively affecting the population of acetoclastic microorganisms means that even if the population of acetogenic microorganisms changes, the population of acetoclastic microorganisms experiences a greater change.

Syngas Generation

The source of the syngas is not critical to the broad aspects of this invention. Gasification, partial oxidation, and reforming (autothermal and steam) of biomass or fossil carbonaceous materials can be used. Gasification and partial oxidation processes are disclosed in United States Published Patent Application No. 20130137151. Rice, et al, in "Autothermal Reforming of Natural Gas to Synthesis Gas", Reference: KBR Paper #2031, Sandia National Laboratories, April 2007, discuss autothermal reforming and conditions. Steam reforming is a widely practiced commercial unit operation. See Logdberg, et al., "Natural Gas Conversion", Haldor Topsoe publication (undated). Reforming in the presence of carbon dioxide is known as carbon dioxide reforming with the partial pressure of carbon dioxide causing a shift in the product distribution of the reforming. See, for instance, Madsen, et al, "Industrial Aspects of $CO_2$-reforming", Paper No. 28f, presented at the AIChE Spring Meeting, Houston, Tex., March 1997. Reforming is a temperature dependent equilibrium reaction, and thus the addition of hydrogen, carbon monoxide or carbon dioxide will affect the distribution of steam, hydrogen, carbon monoxide and carbon dioxide from the fresh feed although the distribution in the produced syngas will be set by the thermodynamic equilibria.

Where a source of carbon dioxide is available, steam reforming is generally preferred due to the high hydrogen concentration of the produced syngas and the relative absence of contaminants that must be removed to prevent deleterious effects on the microorganisms for the anaerobic bioconversion to alcohol. Additionally, steam reforming, being non-oxidative, provides a syngas that is relatively free of nitrogen which would be present in the syngas produced by a partial oxidation or autothermal reforming process using air or enriched air as the oxygen source. Another advantage of steam reforming is that the depleted gas phase from the bioreactors can be used as a portion of the fuel required for providing the heat for the steam reforming. By using the depleted gas phase to provide heat, and offset of fresh carbonaceous feed occurs and thereby enhances the net conversion of fresh carbonaceous feed to oxygenated organic compounds. The portion of the carbonaceous feed that can be offset will depend upon the volume and heating value of the depleted gas phase.

Since the unit operations to make the syngas can vary widely, it is understood that the compositions of the syngas may similarly vary widely including the presence of components other than hydrogen, carbon monoxide and carbon dioxide, which components may be inert such as nitrogen and methane or components that may have to be removed due to potential adverse effects on the microorganisms such as hydrogen cyanide. Processes for removing adverse components include those disclosed in United States Published Patent Application Nos. 20130137151; 20130266997; and 20130337513; and U.S. Pat. No. 7,927,513 and U.S. Pat. No. 8,303,849. Also, the relative ratios among hydrogen, carbon monoxide and carbon dioxide may vary widely.

In some instances, more than one source of syngas may be used, and it may be desired to use different types unit operations, e.g., a steam reformer and an autothermal reformer or partial oxidation unit or gasifier, to produce syngas so as to provide the desired overall gas substrate composition. The different types of unit operations may be parallel or may be sequential, i.e., the different unit operation to generate syngas occurs in the presence of syngas from another unit operation.

Although the process for generating the syngas can be selected to provide a desired carbon dioxide partial pressure in the depleted gas phase from the aqueous fermentation broth, such selection is not critical to the methods of this invention as the composition of the syngas can be changed and other techniques can be used to adjust the carbon dioxide partial pressure as is discussed below.

Oxygenated Organic Compounds, Microorganisms and Fermentation Conditions:

The oxygenated organic compounds produced by the processes of this invention will depend upon the microorganism or combination of microorganisms used for the fermentation and the conditions of the fermentation. One or more microorganisms may be used in the fermentation broth to produce the sought oxygenated organic compound or mixture.

Bioconversions of CO and $H_2/CO_2$ to acetic acid, n-butanol, butyric acid, ethanol, propanol, propionate anion and other products are well known. For example, biochemical pathways and energetics of such bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of Biochemistry and Physiology of Anaerobic Microorganisms, L. G. Ljungdahl eds. Springer (2003). Any suitable microorganisms that have the ability to convert the syngas components: CO, $H_2$, $CO_2$ individually or in combination with each other or with other components that are typically present in syngas may be utilized. Suitable microorganisms and/or growth conditions may include those disclosed in U.S. Published Patent Application 20070275447, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; U.S. Pat. No. 7,704,723 entitled "Isolation and Characterization of Novel Clostridial Species," which discloses a biologically pure culture of the microorganism *Clostridium ragsdalei* having all of the identifying characteristics of ATCC No. BAA-622. *Clostridium carboxidivorans* may be used, for example, to ferment syngas to ethanol and/or n-butanol. *Clostridium ragsdalei* may be used, for example, to ferment syngas to ethanol.

Suitable microorganisms and growth conditions include the anaerobic microorganisms *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include: *Clostridium Ljungdahlii*, with strains having the identifying characteristics of ATCC 49587 (U.S. Pat. No. 5,173,429) and ATCC 55988 and 55989 (U.S. Pat. No. 6,136,577) that will enable the production of ethanol as well as acetic acid; *Clostridium autoethanogemum* sp. nov., an anaerobic *bacterium* that produces ethanol from carbon monoxide. Jamal Abrini, Henry Naveau, Edomond-Jacques Nyns, Arch Microbiol., 1994, 345-351; Archives of Microbiology 1994, 161: 345-351; and *Clostridium Coskatii* having the identifying characteristics of ATCC No. PTA-10522 U.S. Pat. No. 8,143,037.

Pathways for the production of oxygenated organic compounds having three carbons include, but are not limited to, *Propionibacterium* species (*Propionibacterium acidipropionici, Propionibacterium acnes, Propionibacterium cyclohexanicum, Propionibacterium freudenreichii, Propionibacterium freudenreichii shermanii, Propionibacterium pentosaecum*) and several other anaerobic bacteria such as *Desulfobulbus propionicus, Pectinatus frisingensis, Pelobacter propionicus, Veillonella, Selenomonas, Fusobacterium, Bacteroides fragile, Prevotella ruminicola, Megasphaera elsdenii, Bacteroides vulgates*, and *Clostridium*, in particular *Clostridium propionicum*.

Mixed cultures of anaerobic microorganisms useful for the bioconversions of syngas to oxygenated organic compounds as has been discussed above. The mixed cultures can be syntrophic and involve C1-fixing microorganisms and microorganisms that bioconvert the products to the C1-fixing microorganisms to higher oxygenated organic compounds. C1-fixing microorganisms include, without limitation, homoacetogens such as *Clostridium ljungdahlii, Clostridium autoethanogenum, Clostridium ragsdalei*, and *Clostridium coskatii*. Additional C1-fixing microorganisms include *Alkalibaculum bacchi, Clostridium thermoaceticum*, and *Clostridium aceticum*.

For instance, Enzien, et al., in United States Published Patent Application 20140206052 A1 disclose methods for producing butanol using C1-fixing homoacetogenic microorganisms and C4-producing butyrogens. See also, Datta, et al., United States Published Patent Application 20140206066 A1. Suitable butyrogens include any microorganisms that contain either or both of the BuCoAAT pathway and BuK pathway and can grow on acetate and ethanol or on acetate and hydrogen as typically found in syngas. Butyrogens known to grow exclusively on ethanol, acetate or syngas include *Clostridium kluyveri, Clostridium carboxidivorans,* and *Butyribacterium methylotrophicum.*

Syntrophic C3-producing microorganisms capable of growing on ethanol and/or acetate as their primary carbon source include, but are not limited to, *Pelobacter propionicus, Clostridium neopropionicum, Clostridium propionicum, Desulfobulbus propionicus, Syntrophobacter wolinii, Syntrophobacter pfennigii, Syntrophobacter fumaroxidans, Syntrophobacter sulfatireducens, Smithella propionica, Desulfotomaculum thermobenzoicum* subspecies *thermosymbioticum, Pelotomaculum thermopropionicum,* and *Pelotomaculum schinkii.*

Suitable microorganisms for bioconversion of syngas to oxygenated organic compounds generally live and grow under anaerobic conditions, meaning that dissolved oxygen is essentially absent from the fermentation liquid (usually the dissolved oxygen content is less than about 0.5 milligrams per liter). Adjuvants to the fermentation broth may comprise buffering agents, trace metals, vitamins, salts etc. Adjustments in the fermentation broth may induce different conditions at different times such as growth and non-growth conditions which will affect the productivity of the microorganisms. U.S. Pat. No. 7,704,723, hereby incorporated by reference in its entirety, discloses the conditions and contents of suitable aqueous broths for bioconversion CO and $H_2/CO_2$ using anaerobic microorganisms.

Anaerobic fermentation conditions include a suitable temperature, say, between 25° and 60° C., frequently in the range of about 30° to 40° C. The conditions of fermentation, including the density of microorganisms, the fermentation broth composition, and syngas residence time, are preferably sufficient to achieve the sought conversion efficiency of hydrogen and carbon monoxide and will vary depending upon the design of the bioreactor and its operation. The pressure may be subatmospheric, atmospheric or super atmospheric, and is usually in the range of from about 90 to 1000 KPa absolute and in some instances higher pressures may be desirable for biofilm fermentation bioreactors. As most bioreactor designs, especially for commercial scale operations, provide for a significant height of fermentation broth for the fermentation, the pressure will vary within the bioreactor based upon the static head.

The fermentation conditions are preferably sufficient to effect at least about 85, preferably at least about 90, mole percent of the total hydrogen and carbon monoxide in the substrate gas fed to the bioreactor assembly to oxygenated organic compounds. As stated above, a combination of bubble size and duration of contact with the fermentation broth are necessary to achieve these high conversions. However, the ease and ability to achieve these high conversions is also dependent upon having the specified electron to carbon ratios. For commercial operations, the fermentation operation preferably provides a total molar conversion of hydrogen and carbon monoxide in the substrate gas feed in the range of at least about 93, preferably at least about 97, mole percent. If required to provide adequate contact time between the gas bubbles and the aqueous fermentation broth, more than one bioreactor may be used in gas flow series in the bioreactor assembly. The use of sequential, deep tank bubble column bioreactors is disclosed in United States Published Patent Application 20130078688.

The rate of supply of the gas feed under steady state conditions to a bioreactor is preferably such that the rate of transfer of carbon monoxide and hydrogen to the liquid phase matches the rate that carbon monoxide and hydrogen are bioconverted. The rate at which carbon monoxide and hydrogen can be consumed will be affected by the nature of the microorganism, the concentration of the microorganism in the fermentation broth and the fermentation conditions. Conditions affecting the rate of transfer such as interfacial surface area between the gas and liquid phases and driving forces are important to the rate of mass transfer of carbon monoxide and hydrogen to the broth.

Preferably the substrate gas is introduced into the bioreactor in the form of microbubbles. Often the microbubbles have diameters in the range of 0.01 to 0.5, preferably 0.02 to 0.3 millimeter. Preferably the substrate gas is injection using a motive fluid. Variations in the motive liquid flow rate can be used to modulate the microbubble size and thus modulate the rate of transfer of carbon monoxide and hydrogen to the liquid phase. Moreover, the modulation provides microbubbles that provide a stable gas-in-liquid dispersion. The injectors may be jet mixers/aerators or slot injectors. Slot injectors are preferred, one form of which is disclosed in U.S. Pat. No. 4,162,970. These injectors operate using a motive liquid. The injectors, especially slot injectors, are capable of operating over a wide range of liquid and gas flow rates and thus are capable of significant turn down in gas transfer capability. The injectors are characterized as having nozzles of at least about 1, often about 1.5 to 5, say, 2 to 4, centimeters as the cross-sectional dimension in the case of jet injectors or as the smaller cross-sectional dimension in the case of slot injectors. The bubble size generated by the injectors will be influenced by, among other factors, the rate of liquid flow through the injector and the ratio of gas phase to liquid phase passing through the injector as well as characteristics of the broth itself including, but not limited to its static liquid depth. See also, United States Published Patent Application 20130078688. In some instances the microbubbles which form a less dense gas-liquid dispersion and any motive fluid used to generate the microbubbles, can facilitate liquid mixing in a bioreactor.

Bioreactor Assembly

The bioreactor assembly may comprise one or more bioreactors which may be, with respect to gas flow, in parallel or in series flow. The bioreactor assembly contains a bioreactor that is characterized as having a substantially uniform aqueous phase composition and a substantially non-uniform substrate concentration. Where more than one bioreactor is used in gas flow series, at least the terminal bioreactor in the series has this characterization. Representative of bioreactors include, but are not limited to, bubble column bioreactors; jet loop bioreactors; stirred tank bioreactors; trickle bed bioreactors; biofilm bioreactors; moving bed bioreactors; membrane bioreactors and static mixer bioreactors including, but not limited to, pipe bioreactors.

Because of economy of capital cost and operation, deep tank bioreactors are preferred. Regardless of the type of deep tank bioreactor, especially where using microbubbles that promote a stable dispersion of bubbles in the broth, mixing currents exist that not only assure the relatively uniform aqueous phase composition but also increase the contact time between the gas bubbles and the broth.

The processes of this invention are particularly attractive for deep tank bubble column bioreactors which are less expensive from cost and operating standpoints than other types of deep tank bioreactors. Where bubble column bioreactors are used, the depth of the aqueous fermentation broth is often at least about 15, say, between about 20 and 30, preferably between about 20 and 25, meters.

Product Recovery

The fermentation vessel may have added from time to time or continuously one or more streams of water, nutrients or adjuvants, and microorganisms. A portion of the broth is withdrawn from time to time or continuously from the bioreactor for product recovery. Usually, the withdrawal is made at a point at the upper portion of the broth. Product recovery can consist of known equipment arrangements for removal of residual cell material, separation and recovery of liquid products from the broth, return of recovered broth and purging of waste streams and materials. Suitable equipment arrangements can include filters, centrifuges, cyclones, distillation columns, membrane systems and other separation equipment. U.S. Pat. No. 8,211,679, herein incorporated by reference in its entirety, shows an arrangement for a product recovery bioreactor that recovers an ethanol product from a bioreactor.

Substrate Depleted Gas Phase and Carbon Dioxide Partial Pressure

The substrate depleted gas phase egressing from the aqueous fermentation broth will contain a small fraction of the hydrogen and carbon monoxide introduced into the bioreactor assembly as the substrate gas and will contain carbon dioxide due to at least one of carbon dioxide being contained in the gas substrate and carbon dioxide being generated by the acetogenic microorganisms producing ethanol. The egressing gas phase will also contain inert components introduced with the substrate gas such as nitrogen and methane and will be saturated with water vapor at the temperature and pressure conditions.

In the methods of this invention, the partial pressure of carbon dioxide in the substrate depleted gas phase above the fermentation broth is adjusted to control the population of acetoclastic microorganisms in the fermentation broth. Below a partial pressure of carbon dioxide of about 3 kPa, the population of acetoclastic microorganisms, if present, is sufficiently low that little contamination of the sought oxygenated organic compound is due to the bioconversion of acetogenic oxygenated organic compounds by the acetoclastic microorganisms to higher oxygenated organic compound. For syntrophic bioconversions, the partial pressure of carbon dioxide is typically within the range of about 1.5 or 2 to 3 kPa. Above 3 kPa, the acetoclastic microorganisms typically are exposed to sufficient carbon dioxide that the ratio between acetogens and acetoclastic microorganisms will be determined by competition between the microorganisms. Preferably the fermentation broth in the bioreactor has substantially uniformity although the gas phase in the fermentation broth may be substantially non-uniform.

A partial pressure of carbon dioxide between about 1.5 or 2 to about 3 kPa selectively affects the population of acetogenic microorganisms and thereby enables a desired ratio of the population of acetoclastic microorganisms to acetogenic microorganisms to be achieved. At partial pressures of carbon dioxide in the lower portion of this range, the cell density of acetoclastic microorganisms is less than that occurring at a partial pressure in the higher portion of this range. (All partial pressures being determined at steady state operating conditions including a stable relative population of acetoclastic and acetogenic microorganisms.) Hence, the cell density ratio between the acetoclastic and acetogenic microorganisms can be adjusted to enhance production of a desired mix of oxygenated organic compounds. Where the higher oxygenated organic compounds are sought, the ratio should provide for the generation of acetate anion and ethanol at about the same rate that the acetoclastic microorganisms are able to bioconvert acetate anion and ethanol to the higher oxygenated organic compound. It should be understood that the bioactivities of different acetogenic and acetoclastic microorganisms can be different, and that the other fermentation conditions can affect the bioconversion rates of each of these types of microorganisms. It is within the skill of an operator based upon this disclosure to empirically determine for a given system where the partial pressure of carbon dioxide should be established to optimize the rate of production of and the mixture of oxygenated organic compound.

In continuous processes to make oxygenated organic compound, the method for controlling the population of acetoclastic microorganisms may be implemented on a continuous or intermittent basis. The method can be implemented intermittently since material changes in the population of acetoclastic microorganisms occur over period of time. The duration of the implementation and its frequency will vary depending upon the population growth rate of the acetoclastic microorganism and the extent that the size of the population needs to be altered.

Where the methods of this invention are used to control the population of acetoclastic microorganisms in a syntrophic bioconversion, continuous implementation of the methods providing a sought carbon dioxide partial pressure in the depleted gas phase are generally preferred. Where the methods of this invention are used to reduce the population of acetoclastic microorganisms, or prevent an infection of acetoclastic microorganisms, in an acetogenic fermentation, intermittent implementation of the methods may be sufficient. In some instances where intermittent implementation of the methods, maintaining the carbon dioxide partial pressure in the depleted gas phase at a level that affects the size of the population of acetoclastic microorganisms occurs for a duration of between about 1 hour to 10 days. The frequency of the implementation of the methods will be a function of the rate of growth of the acetoclastic microorganism population and often the frequency is between about 1 hour and 30 or 60 days.

In many commercial-scale processes to make oxygenated organic compounds, more than one bioreactor is used. The implementation of the methods of this invention can be cycled among the bioreactors such that at least one of the bioreactors has the carbon dioxide partial pressure to control the population of the microorganisms while at least one other bioreactor has a different partial pressure of carbon dioxide in the depleted gas phase. This cycling method is particularly useful for processes for using acetogenic microorganisms for making oxygenated organic compound and minimizing the generation of higher oxygenated organic compounds. As can be readily appreciated, in instances where the composition of the gas substrate is adjusted to provide the sought partial pressure of carbon dioxide in the depleted gas phase, the gas substrate to the other bioreactors need not be altered. Where carbon dioxide is removed from the gas substrate to a bioreactor to achieve the sought partial pressure of carbon dioxide in the depleted gas phase of that bioreactor, the removed gases can optionally be combined with the gas substrate to one or more other bioreactors.

The partial pressure of carbon dioxide in the gas phase above the fermentation broth is affected by the molar concentrations of the gaseous components in the gas phase and the pressure. Although the pressure can be selected over a wide range, the preferred operations use one or more of a sweep gas and adjustment of the gas substrate composition to achieve the sought carbon dioxide partial pressure. In practicing the methods of this invention, consideration needs to be given to the bioconversion activity in the bioreactor as overall cell density and upsets can affect the portion of the substrate that is bioconverted.

Where the gas phase to a bioreactor would result in a higher carbon dioxide partial pressure in the depleted gas phase than is sought, removal of at least a portion of the carbon dioxide in the gas substrate is one technique to adjust the carbon dioxide partial pressure. Any suitable carbon dioxide removal process may be used including amine extraction, alkaline salt extractions, water absorption, membrane separation, adsorptions/desorption, and physical absorption in organic solvents. A preferred process for removal of carbon dioxide from gases is by contacting the gas with an aqueous solution containing oxygenated organic compound. This process for removing carbon dioxide from gas to be fed to a reactor is disclosed in U.S. Pat. No. 8,017,384. See also, U.S. Published Patent Application 2012/0003707.

Another technique to reduce the partial pressure of carbon dioxide in the depleted gas phase is to provide sufficient hydrogen and residence time to increase the $H_2/CO_2$ conversion. Since in many instances the acetogenic microorganism co-produces carbon dioxide, the hydrogen supply rate in the gas should be sufficient to bioconvert both carbon dioxide in the gas substrate supplied to the bioreactor and that co-produced by the carbon monoxide bioconversion. Especially where the sought oxygenated organic compound product is one or more alcohols, the electron to carbon ratio of the gas substrate is preferably in the range of about 5.5:1 to 6.5:1, say, about 5.7:1 to 6.2:1. The carbon monoxide to hydrogen mole ratio is often below about 1.1:1, say, about 0:1 to 1:1. Where hydrogen is required to be added, it can be procured from any suitable source.

EXAMPLE

A pilot plant capable of continuous operation and having a 10 liter anaerobic, continuously stirred fermenter is used to bioconvert a synthesized syngas feed to ethanol and butanol. The syngas is continuously supplied at a substantially constant volumetric rate to the fermenter, and fresh aqueous feed containing nutrients is continuously supplied at the same rate fermentation broth is withdrawn from the fermenter. Exhaust gas is continuously removed from the top of the fermenter at a rate sufficient to maintain a pressure at the top of the fermenter of about 15 kPa.

A mixed culture of *Clostridium autoethanogenum* is prepared in the fermenter by first growing the acetogen to an O.D. of 1.7 on minimal media and syngas with a composition of $H_2$-56%, CO-22%, $CO_2$-5%, and $CH_4$-17% (mol %). Once ethanol and acetate concentrations of 10 and 5 g/L respectively are achieved, a mixed butyrogen (acetoclastic microorganisms) culture is added and the fermenter is operated until the composition of the fermentation broth indicates that the ratios among ethanol, acetate anion, butanol and butyrate anion are stable. The partial pressure of carbon dioxide in the depleted gas phase is in excess of 3 kPa.

The composition of the syngas is then adjusted by reducing the amount of carbon dioxide added to formulate the syngas, but maintaining the syngas flow rate constant, until at steady state the partial pressure of carbon dioxide in the exhaust gas is about 3 kPa. The concentrations of ethanol, acetate anion, butanol and butyrate anion in the fermentation broth remain essentially the same as prior to the adjustment. The composition of the syngas is then further adjusted by reducing the amount of carbon dioxide added to formulate the syngas, but maintaining the syngas flow rate constant, until at steady state the partial pressure of carbon dioxide in the exhaust gas is about 2 kPa. The concentration of ethanol in the fermentation broth increases significantly as the concentration of butanol and butyrate anion drop. The composition of the syngas is once again further adjusted by reducing the amount of carbon dioxide added to formulate the syngas, but maintaining the syngas flow rate constant, until at steady state the partial pressure of carbon dioxide in the exhaust gas is about 1 kPa. The concentration of ethanol in the fermentation broth increases significantly, and the fermentation broth is substantially devoid butanol and butyrate anion.

It is claimed:

1. A continuous process for the anaerobic bioconversion of a gas substrate comprising carbon monoxide and/or hydrogen and carbon dioxide in an aqueous fermentation broth containing at least one acetogenic microorganism suitable for bioconverting said substrate to at least one acetogenic oxygenated organic compound and containing at least one acetoclastic microorganism, which process comprises:
    a) continuously contacting said gas substrate with said aqueous fermentation broth under acidic, anaerobic fermentation conditions to convert the gas substrate to the at least one acetogenic oxygenated organic compound and provide an oxygenated organic compound containing broth and a depleted gas phase;
    b) continuously or intermittently withdrawing a portion of said acetogenic oxygenated organic compound-containing broth for recovery of said acetogenic oxygenated organic compound, said withdrawal being sufficient to maintain the acetogenic oxygenated organic compound in said aqueous fermentation broth below a concentration that unduly adversely affects the at least one acetogenic microorganism; and
    c) continuously or intermittently controlling partial pressure of carbon dioxide in the depleted gas phase from the aqueous fermentation broth at from zero to about 3 kPa to provide a desired population ratio of acetoclastic microorganisms to acetogenic microorganisms.

2. The process of claim 1, wherein the partial pressure of carbon dioxide in the depleted gas phase is continuously controlled at from zero to about 2 kPa to reduce the population of acetoclastic microorganisms contained in the aqueous fermentation broth.

3. The process of claim 2, wherein the acetogenic oxygenated organic compound comprises ethanol.

4. The process of claim 1, wherein the partial pressure of carbon dioxide in the depleted gas phase is intermittently controlled at from zero to about 1 kPa for a duration sufficient to reduce the population of acetoclastic microorganisms contained in the aqueous fermentation broth.

5. The process of claim 1, wherein the partial pressure of carbon dioxide in the aqueous fermentation broth is continuously controlled at from zero to about 1 kPa.

6. The process of claim 1, wherein said gas substrate is continuously contacted with said aqueous fermentation broth in a deep tank bioreactor.

7. The process of claim 1, wherein the partial pressure of carbon dioxide in the depleted gas phase is continuously or intermittently controlled at from zero to about 1.5 kPa to reduce the population of acetoclastic microorganisms contained in the aqueous fermentation broth.

8. The process of claim 7, wherein the acetogenic oxygenated organic compound comprises ethanol.

9. The process of claim 1, wherein the acetogenic oxygenated organic compound comprises ethanol.

10. The process of claim 1, wherein the gas substrate has a mole ratio of carbon monoxide to hydrogen of less than 1.1:1 and an electron to carbon ratio of between 5.5:1 and 6.5:1.

11. The process of claim 1, wherein the gas substrate has a mole ratio of carbon monoxide to hydrogen of less than 0.5:1 and an electron to carbon ratio of between 5.5:1 and 6.5:1.

12. The process of claim 1, wherein the partial pressure of carbon dioxide in the depleted gas phase is continuously controlled.

13. The process of claim 1, wherein the partial pressure of carbon dioxide in the depleted gas phase is intermittently controlled.

\* \* \* \* \*